United States Patent [19]

Engel et al.

[11] 4,424,222
[45] Jan. 3, 1984

[54] PYRIDOBENZODIAZEPINONES, PHARMACEUTICAL COMPOSITIONS AND METHOD OF USE THEREOF

[75] Inventors: Wolfhard Engel; Günther Schmidt, both of Biberach; Günter Trummlitz, Warthausen; Wolfgang Eberlein, Biberach, all of Fed. Rep. of Germany; Rudolf Hammer, Milan; Piero D. Soldato, Monza, both of Italy

[73] Assignee: Karl Thomae GmbH, Biberach an der Riss, Fed. Rep. of Germany

[21] Appl. No.: 462,183

[22] Filed: Jan. 31, 1983

[30] Foreign Application Priority Data

Feb. 9, 1982 [DE] Fed. Rep. of Germany ....... 3204401

[51] Int. Cl.³ .................... A61K 31/55; C07D 471/04
[52] U.S. Cl. .................................. 424/250; 421/256; 421/267; 260/239.3 T
[58] Field of Search ................. 260/239.3 T; 424/250, 424/256, 267

[56] References Cited

U.S. PATENT DOCUMENTS 3,660,380 5/1972 Schmidt et al. ............. 260/239.3 T

Primary Examiner—Robert T. Bond
Attorney, Agent, or Firm—Hammond & Littell, Weissenberger & Muserlian

[57] ABSTRACT

New pyridobenzodiazepinones of the formula

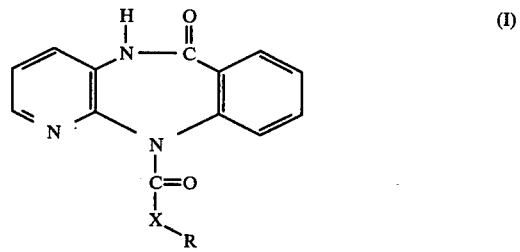

are described wherein X represents oxygen, —NH— or —NCH$_3$— and R represents 1-methyl-4-piperidinyl or 4-methyl-1-piperazinyl group optionally substituted by a methyl group, or a 3α- or 3β-tropanyl group, and the nontoxic pharmaceutically acceptable acid addition salts thereof. The specification also describes processes for preparing these compounds, pharmaceutical compositions containing these compounds and new intermediate products used in preparing them.

The compounds of formula I have antiulcerative effects and an inhibitory effect on gastric acid secretion, without the side effects such as dryness of the mouth and mydriasis which occur with other substances having an anticholinergic activity.

13 Claims, No Drawings

4,424,222

PYRIDOBENZODIAZEPINONES, PHARMACEUTICAL COMPOSITIONS AND METHOD OF USE THEREOF

BACKGROUND OF THE INVENTION

Pyridobenzodiazepinones with antiulcerative and secretion-inhibiting properties have already been described in U.S. Pat. Nos. 3,660,380, 3,691,159, 4,213,984, 4,213,985 and 4,210,648.

It has now been found that the new pyridobenzodiazepinones with novel aminoacyl groups have valuable pharmacological properties which are superior to those of the above mentioned compounds.

OBJECT OF THE INVENTION

It is an object of the invention to provide novel pyridobenzodiazepinones and the nontoxic, pharmaceutically acceptable salts thereof.

It is another object of the invention to provide pyridobenzodiazepinones and nontoxic, pharmaceutically acceptable salts thereof which are useful in the prevention and the treatment of disorders of the stomach and intestines such as ulcers, gastritis and hyperacidity in both humans and animals.

Another object of the invention is to provide suitable intermediates for use in the preparation of the novel pyridobenzodiazepinones.

A further object of the invention is to provide pyridobenzodiazepinones of formula I,

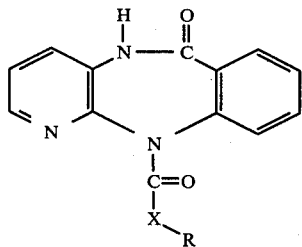

wherein X is oxygen, —NH— or —NCH₃— and R is 1-methyl-4-piperidinyl, 4-methyl-1-piperazinyl, a 3α- or 3β-tropanyl group, each of the groups being optionally substituted by a further methyl group, and optionally the diastereomeric and enantiomeric forms thereof and the nontoxic, pharmaceutically acceptable acid addition salts thereof.

These and other objects of the invention will become more apparent as the description thereof proceeds.

DESCRIPTION OF THE INVENTION

The present invention relates to pyridobenzodiazepinones of formula I

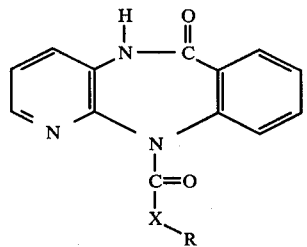

wherein X is oxygen, —NH— or —NCH₃— and R is 1-methyl-4-piperidinyl, 4-methyl-1-piperazinyl, or a 3α- or 3β-tropanyl group, each of the groups being optionally substituted by a further methyl group, and the nontoxic, pharmaceutically acceptable acid addition salts thereof.

The compounds of formula I may also be obtained in the form of their nontoxic, pharmaceutically acceptable salts after being reacted with inorganic or organic acids. Suitable acids include, for example, hydrochloric, hydrobromic, sulphuric, methylsulphuric, phosphoric, tartaric, fumaric, citric, maleic, succinic, gluconic, malic, p-toluenesulphonic, methanesulphonic or amidosulphonic acid.

The following compounds may be mentioned by way of example to illustrate the object of the invention:

5,11-dihydro-11-[[(1-methyl-4-piperidinyl)oxy]carbonyl]-6H-pyrido[2,3-b][1,4]benxodiazepin-6-one, cis-5,11-dihydro-11-[[(1,2-dimethyl-4-piperidinyl)oxy]-carbonyl]-6H-pyrido[2,3-b][1,4]benzodiazepin-6-one, trans-5,11-dihydro-11-[[(1,2-dimethyl-4-piperidinyl)oxy]carbonyl]-6H-pyrido[2,3-b][1,4]benzodiazepin-6-one, cis-5,11-dihydro-11-[[(1,3-dimethyl-4-piperidinyl)oxy]-carbonyl]-6H-pyrido[2,3-b][1,4]benzodiazepin-6-one, trans-5,11-dihydro-11-[[(1,3-dimethyl-4-piperidinyl)oxy]carbonyl]-6H-pyrido[2,3-b][1,4]benzodiazepin-6-one, 5,11-dihydro-5-[[(1-methyl-4-piperidinyl)amino]carbonyl]-6H-pyrido[2,3-b][1,4]benzodiazepin-6-one, cis-5,11-dihydro-11-[[(1,2-dimethyl-4-piperidinyl)amino]carbonyl]-6H-pyrido[2,3-b][1,4]benzodiazepin-6-one, trans-5,11-dihydro-11-[[(1,2-dimethyl-4-piperidinyl)amino]carbonyl]-6H-pyrido[2,3-b][1,4]benzodiazepin-6-one, cis-5,11-dihydro-11-[[(1,3-dimethyl-4-piperidinyl)amino]carbonyl]-6H-pyrido[2,3-b][1,4]benzodiazepin-6-one, trans-5,11-dihydro-11-[[(1,3-dimethyl-4-piperidinyl)amino]carbonyl]-6H-pyrido[2,3-b][1,4]benzodiazepin-6-one, 5,11-dihydro-11-[[(4-methyl-1-piperazinyl)-amino]carbonyl]-6H-pyrido[2,3-b][1,4]benzodiazepin-6-one, 5,11-dihydro-11-[[(3,4-dimethyl-1-piperazinyl)-amino]-carbonyl]-6H-pyrido[2,3-b][1,4]benzodiazepin-6-one, 5,11-dihydro-11-[[(2,4-dimethyl-1-piperazinyl)amino]-carbonyl]-6H-pyrido[2,3-b][1,4]benzodiazepin-6-one, 5,11-dihydro-11-[[(4-methyl-1-piperazinyl)oxy]carbonyl]-6H]pyrido[2,3-b][1,4]benzodiazepin-6-one, 5,11-dihydro-11-[[(3,4-dimethyl-1-piperazinyl)oxy]carbonyl]-6H-pyrido[2,3-b][1,4]benzodiazepin-6-one, 5,11-dihydro-11-[[(2,4-dimethyl-1-piperazinyl)oxy]carbonyl]-6H-pyrido[2,3-b][1,4]benzodiazepin-6-one, endo-5,11-dihydro-11-[[(8-methyl-8azabicyclo[3,2,-1]oct-3-yl)-oxy]-carbonyl]-6H-pyrido[2,3-b][1,4]benzodiazepin-6-one, exo-5,11-dihydro-11-[[(8-methyl-8-azabicyclo[3,2,1]oct-3-yl)-oxy]-carbonyl]-6H-pyrido[2,3-b][1,4]benzodiazepin-6-one, endo-5,11-dihydro-11-[[(8-methyl-8-azabicyclo[3,2,-1]oct-3-yl)-oxy]carbonyl]-6H-pyrido[2,3-b][1,4]benzodiazepin-6-one, exo-5,11-dihydro-11-[[(8-methyl-8-azabicyclo[3,2,1]oct-3-yl)-amino]carbonyl]-6H-pyrido[2,3-b][1,4]benzodiazepin-6-one, 5,11-dihydro-11-[[N-methyl-N-(1-methyl-4-piperidinyl)amino]carbonyl]-6H-pyrido[2,3-b][1,4]benzodiazepin-6-one, cis-5,11-dihydro-11-[[N-methyl-N-(1,2-dimethyl-4-piperidinyl)-amino]carbonyl]-6H-pyrido[2,3-b][1,4]benzodiazepin-6-one, trans-5,11-dihydro-11-[[N-methyl-N-(1,2-dimethyl-4-piperidinyl)-amino]carbonyl]-6H-pyrido[2,3-b][1,4]benzodiazepin-6-one, cis-5,11-dihydro-11-[[N-methyl-N-(1,3-dimethyl-4-piperidinyl)-amino]carbonyl]-6H-pyrido[2,3-b][1,4]-benzodiazepin-6-one, trans-5,11-dihydro-11-[[N-methyl-N-(1,3-dimethyl-4-piperidinyl)-amino]carbonyl]-6H-pyrido[2,3-b][1,4]benzodiazepin-6-one, 5,11-dihydro-11-[[N-methyl-N-(4-methyl-1-piperazinyl)amino]carbonyl]-6H-pyrido[2,3-b][1,4]benzodiazepin-6-one, 5,11-dihydro-11-[[N-methyl-N-(3,4-dimethyl-1-piperazinyl)amino]-carbonyl]-6H-pyrido[2,3-b][1,4]benzodiazepin-6-one, 5,11-dihydro-11-[[N-methyl-N-(2,4-dimethyl-1-piperazinyl)amino]carbonyl]-6H-pyrido[2,3-b][1,4]-benzodiazepin-6-one, The invention further relates to the pyridobenzodiazepinones of formula Ia used as intermediate products,

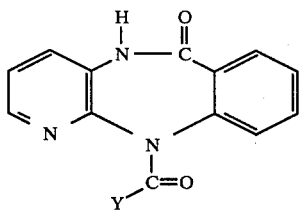

(Ia)

wherein Y represents halogen, preferably bromine or chlorine, or $OR_1$ wherein $R_1$ represents an optionally halogen substituted alkyl group having 1 to 5 carbon atoms, a phenyl group optionally substituted by halogen or nitro or an aralkyl group with 7 to 15 carbon atoms.

$R_1$ is, for example, methyl, ethyl, n-butyl, isobutyl, benzyl, 9-fluorenylmethyl, phenyl, 4-nitrophenyl, 2,2,2-trichloroethyl, 2,4,5-trichlorophenyl or 2,2,2-trichloro-tert. butyl group.

The invention further relates to pharmaceutical compositions which contain one or more pyridobenzodiazepinones of formula I or the physiologically acceptable salts thereof.

For this, the compounds of general formula I can be incorporated in the manner known per se in the conventional pharmaceutical forms, e.g. in solutions, suppositories, tablets, coated tablets, capsules or infusions. The daily dose for oral administration is generally between 0.01 and 5, preferably between 0.02 and 2.5, more particularly between 0.05 and 1.0 mg/kg of body weight, generally administered in the form of several, preferably from 1 to 3 individual doses to achieve the desired results.

The substituted pyridobenzodiazepinones of formula I and the nontoxic, pharmaceutically acceptable acid addition salts thereof have valuable properties which make them commercially viable, and are characterized in particular by an excellent protective effect on the stomach and intestines in warm-blooded animals; for example, they inhibit the formation of gastric ulcers. Moreover, they have a useful therapeutic range, thanks to their low toxicity and the absence of any significant side effects.

The excellent activity of the substituted pyridobenzodiazepinones of formula I and of their pharmaceutically, i.e. biologically, acceptable acid addition salts make it possible to use them in both human and veterinary medicine, for the treatment and prophylaxis of diseases based on disorders of the stomach or intestines. They may be used, for example, to treat acute and chronic gastric and duodenal ulcers, gastritis and gastric hyperacidity in humans and animals.

If the substituted pyridobenzodiazepinones of formula I according to the invention and/or the nontoxic, pharmaceutically acceptable acid addition salts thereof are to be used to treat the diseases mentioned above, the pharmaceutical compositions may also contain one or more pharmacologically active ingredients from other groups of medicaments, such as antacids, e.g. aluminium hydroxide or magnesium aluminate; secretion inhibitors, such as $H_2$ blockers, e.g. cimetidine or ranitidine; gastric and intestinal therapeutic agents, e.g. metaclopramide, bromoprid and tiaprid; tranquillizers such as benzodiazepines, for example diazepam and oxazepam; spasmolytics, e.g. bietamiverine, camylofine; anticholinergics, e.g. oxyphencyclimine and phencarbamide; glucocorticoids such as prednisolone, fluocortolone and betamethasone; non-steroidal antiphlogistic agents such as arylacetic acids and arylpropionic acids, heteroarylacetic acids and heteroarylpropionic acids, benzothiazines carboxamide dioxides, pyrazolidinediones, quinazolinones, e.g. ibuprofen, naproxen, diclofenac, fenbufen, flurbiprofen, indomethacin, lonazolac, sudoxicam, piroxicam, phenylbutazone, bumadizon-calcium, proquazone; local anaesthetics such as tetracaine and procaine; and optionally also enzymes, vitamins, amino acids, etc.

According to the invention, the new pyridobenzodiazepinones of formula I can be obtained by the following processes:

(a) reacting a pyridobenzodiazepinone of formula Ia,

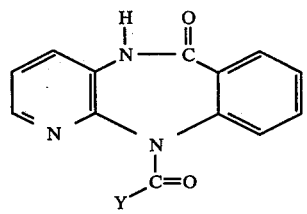

(Ia)

wherein Y is halogen, preferably bromine or chlorine, or $OR_1$, wherein $R_1$ is an optionally halogensubstituted alkyl group with 1 to 5 carbon atoms, a phenyl group optionally substituted by halogen, nitro or an aralkyl group with 7 to 15 carbon atoms, with compounds of formula II $$H-X-R \qquad (II),$$

wherein X and R are as hereinbefore defined.

The reaction is carried out without, or preferably, in the presence of inert solvents (ie with respect to the reactants), e.g. water, toluene or alcohols such as methanol, ethanol or isopropanol, but preferably in the presence of aprotic polar solvents, e.g. tetrahydrofuran, 1,4-dioxane, acetonitrile, N,N-dimethylformamide, dimethylsulphoxide, hexamethylphosphoric acid triamide, or mixtures thereof, and at temperatures between 0°

C. and the boiling point of the reaction mixture, preferably between 40° and 100° C. It has proved helpful to use additional inorganic or organic bases, e.g. alkali or alkaline earth metal hydroxides, alkoxides or carbonates, e.g. sodium hydroxide, sodium methoxide, potassium tert. butoxide, sodium carbonate, potassium carbonate; tertiary amines, e.g. triethylamine, ethyl diisopropylamine, N,N-dimethylaniline or pyridine; and to perform the reaction in the presence of an excess of a compound of formula II.

The reaction may, however, also be carried out with a metal compound of formula IIa,

   (IIa)

wherein M represents an alkali metal atom or one equivalent of an alkaline earth metal atom. Metal compounds of general formula IIa can readily be prepared in situ from compounds of formula II be reacting with alkali metals or alkaline earth metals, e.g. with sodium, potassium or barium, or with alkali metal or alkaline earth metal hydrides, e.g. with sodium, potassium or calcium hydride, or by reacting with alkali or alkaline earth organometallic compounds, e.g. with n-butyl-lithium or phenyllithium.

(b) Reacting 5,11-dihydro-6H-pyrido[2,3-b][1,4]benzodiazepin-6-one with a chlorocarbonic acid derivative of formula IV,

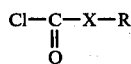   (IV)

or with an isocyanate of formula IVa

   (IVa)

wherein R and X are as hereinbefore defined.

The reaction is preferably carried out in inert organic solvents, for example, in aromatic hydrocarbons such as toluene, xylene, in ethers such as diisopropyl ether, tetrahydrofuran or dioxane, in ketones such as pentan-3-one, in chlorinated aliphatic hydrocarbons, such as 1,2-dichloroethane or in other solvents such as acetonitrile or dimethylformamide or in mixtures thereof, optionally in the presence of tertiary organic bases such as pyridine, and at temperatures up to the boiling point of the reaction mixture, preferably at temperatures between +30° and +100° C.

Bases of formula I thus obtained can subsequently be converted into the acid addition salts thereof or any acid addition salts obtained may be converted into the free bases or other nontoxic, pharmaceutically acceptable acid addition salts.

Some of the pyridobenzodiazepinones of formula I according to the invention contain one or more asymmetric carbon atoms in the side chain —CO—X—R. These compounds may therefore occur in two diastereomeric cis and trans forms or as the enantiomeric (+) and (−) forms. The invention include the individual isomers and the mixtures thereof.

The diastereomers can be separated on the basis of their different physico-chemical properties, e.g. by fractional recrystallisation from suitable solvents, by high pressure liquid chromatography or gas chromatography. Only one diastereomer is obtained in each case if the methods of synthesis described above are carried out with only one diastereomer of formula II or IIa.

Any racemates of the compounds of formula I may be separated according to known methods, for example using an optionally active acid such as (+)- or (−)-tartaric acid or a derivative thereof, such as (+)- or (−)-diacetyl tartaric acid, (+)- or (−)-monomethyl tartrate or (+)-camphorsulphonic acid.

In a conventional method for separating isomers, the racemate of a compound of formula I is reacted with an equimolar quantity of one of the above mentioned optically active acids in a solvent and the crystalline optically active salts obtained are separated on the basis of their different solubilities. This reaction may be carried out in any type of solvent provided that the salts have sufficiently different solubilities therein. Preferably, methanol, ethanol or a mixture thereof, for example in proportions of 50:50 by volume, is used. Then each of the optically active salts is dissolved in water, neutralized with a base such as sodium carbonate or potassium carbonate and in this way the corresponding free compound is obtained in the (+) or (−) form.

Only one enantiomer is obtained in each case if the methods of synthesis described above are carried out with only one enantiomer of formula II or IIa.

The new compounds of formula Ia required as intermediate products are obtained, according to the invention, by reacting the known 5,11-dihydro-6H-pyrido[2,3-b][1,4]benzodiazepin-6-one (see U.S. Pat. No. 3,406,168) with a halocarbonic acid derivative of general formula III,

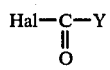   (III)

wherein Hal represents bromine or chlorine, preferably the chlorine, and Y is as hereinbefore defined.

The reaction is carried out in inert organic solvents, such as aromatic hydrocarbons, e.g. toluene, chlorobenzene or xylene; open-chained or cyclic ethers, such as diisopropylether, tetrahydrofuran or dioxane; open-chain or cyclic aliphatic ketones, for example pentan-3-one; chlorinated aliphatic hydrocarbons, such as 1,2-dichloroethane or other solvents such as acetonitrile or dimethylformamide or mixtures thereof and in the presence of tertiary organic bases, preferably pyridine, and at temperatures up to, at most, the boiling point of the solvent or mixture of solvents used, preferably between +30° and +80° C.

The starting compounds of formula II are known or may be prepared analogously to processes described in the literature. For example, 1-hydroxy-4-methylpiperazine is obtained as described by S. M. Riba, A. S. Issa and Y. A. Beltagy, Pharmazie 33, 711 (1978), by reacting bis[N-(2-chloroethyl)]-methylamine with hydroxylamine hydrochloride in an aqueous ethanol solution and in the presence of potassium carbonate, 3α-aminotropane and 3α-methylaminotropane are obtained according to S. Archer et al., J. Amer. Chem. Soc. 79, 4194-4198(1957); 3β-aminotropane is obtained according to R. Willstatter et al, Ber. dtsch. chem. Ges. 31, 1202 (1898); pseudotropine is obtained according to J. J. Tufariello et al., J. Amer. Chem. Soc. 101, 2435-2442 (1979).

Halocarbonic acid derivatives of formula III are known.

Chlorocarbonic acid derivatives of formula IV and isocyanates of formula IVa are known or can be obtained using methods described in the literature (cf. for example I. W. Mathison et al., J. Pharm. Sci. 62, 158 [1963]; H. Hopff and H. Ohlinger, Angew. Chem. 61, 183 [1949]; W. Siefken, Liebigs Ann. Chem. 562, 75 [1949]; Houben-Weyl VIII, 117; Ullmann V, 72; L. C. Raiford and K. Alexander, J. Org. Chem. 5, 306 [1940]; H. H. Saunders and R. J. Slocombe, Chem. Rev. 43, 203 [1949]; R. J. Slocombe, E. E. Hardy, J. H. Saunders and R. L. Jenkins, J. Amer. chem. Soc. 72, 1888 [1950]; H. Habad and A. G. Zeiler, Chem. Rev. 73, 75 [1973].

As already mentioned hereinbefore, the new compounds of formula I have valuable pharmacological properties; in particular, they have antiulcerogenic effects and they inhibit gastric acid secretion and they have favourable effects on various other disorders of the gastrointestinal tract, including, in particular, irritable colon.

A favorable balance between antiulcerogenic and antisecretory effects, on the one hand, and the undesirable effects on pupil size and the secretion of tears and saliva, on the other hand, which occurs particularly with therapeutic agents having an anticholinergic component, is of particular importance in the therapeutic use of the substances. The following tests show that the compounds according to the invention have surprisingly favorable characteristics in this respect.

INVESTIGATION OF THE SELECTIVITY OF THE ANTIMUSCARINIC ACTIVITY

Aims:

Oxotremorine, a specific agonist for muscarinic receptors, produces lesions in the mucous membrane of the stomach in rats and increases their secretion of saliva. This test method was chosen so that any selective activity of an intimuscarinic substance on the stomach could be identified.

Method:

10 female albino rats (of the Crl:COBS-CD (SD) BR strain) with a body weight of from 120 to 150 g were used in each treatment group and were kept without food for 24 hours before the start of the test but given free access to drinking water.

In order to determine, in preliminary tests, the muscarinic effect of oxotremorine on each of the symptoms studied, a dosage/activity curve was drawn up with at least three dosages for each symptom.

When testing the antimuscarinic substances, the dosage of oxotremorine which triggered the symptom in question in 90 to 100% of the animals in the preliminary tests was used.

Lesions in mucous membrane of stomach: 0.62 mg/kg i.v.

Secretion of saliva: 0.083 mg/kg i.v.

Each antimuscarinic substance was administered intravenously in uniformly graduated doses 15 minutes before the oxotremorine was administered. Control groups were given corresponding quantities of the solvent and suspending agent without the test substance.

Immediately after the oxotremorine was administered, the animals were placed in a glass case for 15 minutes and observed.

The test for the effect on the oxotremorine-induced secretion of saliva was carried out as a double blind test, i.e. the tester did not know which treatment the animals had been given.

The results were expressed as the percentage inhibition of the oxotremorine effect (the percentage of animals which did not show the sympton in question). The $ED_{50}$ values were determined using the method described by LITCHFIELD and WILCOXON (J. Pharmacol. Exp. Ther. 96, 99, 1949).

The effects on lesions of the mucous membrane of the stomach were evaluated as follows:

The lesions of the gastric mucous membrane were produced by intravenous injection of 0.62 mg/kg of oxotremorine 30 minutes after the oral administration of 1 mg/kg of neostigmine (a cholinesterase inhibitor). 60 minutes after the administration of the neostigmine, the animals were killed, the stomachs were removed and opened and examined for the presence of any lesions in the mucous membrane. The protective effect of the test substances was expressed as the percentabge inhibition (percentage of animals without lesions). The $ED_{50}$ and $ED_{70}$ values were determined using the method of LITCHFIELD AND WILCOXON (see above).

Mydriasis

The effect of the test substances on the pupil size in rats was investigated as follows:

The substances were administered intravenously to groups of 10 animals in at least three uniformly graduated doses. The pupil size was then observed for 10 minutes to see if there were any changes (mydriasis or miosis) and again the test was carried out double blind, i.e. the tester did not know what preliminary treatment the animals had received. The percentage of test animals in which mydriasis occurred was determined. The $ED_{50}$ values were again determined using the method of LITCHFIELD and WILCOXON (see above).

STUDIES OF BINDING TO MUSCARINIC RECEPTORS: DETERMINATION OF THE $IC_{50}$ VALUE

The organ donors were male Sprague-Dawley rats with a body weight of from 180 to 200 g. After the heart, stomach and cerebral cortex had been removed, the remainder of the operation was carried out in ice-cold Hepes-HCl buffer (pH 7.4; 100 m molar NaCl, 10 m molar $MgCl_2$). The smooth muscle of the fundus of the stomach was separated from the mucous membrane of the stomach and subjected to preliminary homogenization. The whole heart was cut up with scissors. All the organs were then homogenized in a Potter apparatus.

For the binding test, the homogenized organs were diluted as follows:

Smooth muscle of the fundus of the stomach: 1:100

Whole heart: 1:250

Cerebral cortex: 1:3000

The homogenized organ preparations were incubated at a specific concentration of a radio labeled compound and with a series of concentrations of the non-radioactive test substances in an Eppendorf centrifuge tube at 30° C. Then duration of incubation was 45 minutes. 0.3 n molar $^3$H-N-methylscopolamine ($^3$H-NMS) was used as the radio labeled compound. After incubation had been brought to an end by centrifuging at 14 000 g, the radioactivity in the pellet was determined. It represents the sum of the specific and non-specific binding of $^3$H-NMS. The proportion of non-specific binding was defined as the radioactivity which was bound in the presence of $1\mu$ molar quinuclidinylbenzylate. Four measurements were taken in each case. The $IC_{50}$ values of the non-labelled test substances were determined graphically. They represent the concentration of test substance at which the specific binding of $^3$H-NMS to the muscarinic receptors in the various organs was inhibited by 50%.

The following compounds were tested, for example, according to the method described above:

A = 5,11-dihydro-11-[[(1-methyl-4-piperidinyl)oxy]carbonyl]-6H-pyrido[2,3,-b][1,4]benzodiazepin-6-one B = 5,11-dihydro-11-[[(1-methyl-4-piperidinyl)amino]carbonyl]-6H-pyrido[2,3-b][1,4]benzodiazepin-6-one and C = 5,11-dihydro-11-[[(4-methyl-1-piperazinyl)amino]carbonyl]-6H-pyrido]2,3-b][1,4]benzodiazepin-6-one.

Results

| | Receptor binding tests $IC_{50}$ [n mol $1^{-1}$] | | | Oxotremorine Test [μg/kg i.v. Anti-ulcerative effect] | | Inhibition of salivation | Mydriasis $ED_{50}$ |
|---|---|---|---|---|---|---|---|
| Substance | Cortex | Smooth muscle fundus of stomach | Heart | $ED_{50}$ | $ED_{70}$ | $ED_{50}$ | [μg/kg i.v.] |
| A | 100 | ca. 900 | 500 | 10 | 30 | 850 | 130 |
| B | 200 | 1200 | | 6.8 | 19 | 420 | 139 |
| C | 60 | 900 | | 3.3 | 5.2 | 56 | 70 |

The results in the above table show that the compounds mentioned generally have a high affinity to muscarinic receptors. Moreover, the results show that the new compounds of formula I differentiate between muscarinic receptors in different types of tissue. This is clear from the considerably lower $IC_{50}$ values in the tests on preparations from the cerebral cortex compared with those of the smooth muscle of the stomach and heart.

The pharmacological data in the above table show—in complete agreement with the receptor binding studies—that the formation of oxotremorine-induced lesions in the mucous membrane of the stomach is inhibited by the abovementioned compounds even at doses at which no restriction of salivation and no mydriasis can be observed.

The following examples are given by way of illustration and not by way of limitation.

EXAMPLES

The following Examples serve to illustrate the invention in more detail. "M.p." indicates "melting point", "D" indicates "decomposition".

Example 1

5,11-dihydro-11-[[(1-methyl-4-piperidinyl)amino]carbonyl]-6H-pyrido[2,3-b][1,4]benzodiazepin-6-one 3.6 g (0.013 mol) of 11-chlorocarbonyl-5,11-dihydro-6H-pyrido[2,3-b][1,4]benzodiazepin-6-one and 1.4 g (0.013 mol) of sodium carbonate were refluxed for 3 hours in 80 ml of anhydrous ethanol together with 1.75 g (0.016 mol) of 4-amino-1-methyl-piperidine. The mixture was filtered while hot, the filtrate was cooled and the substance which crystallized out was suction filtered. The crude product obtained was recrystallized from anhydrous ethanol.

Colorless crystals, M.p. 144°–147° C.
Yield: 73% of theory.

The following were obtained analogously:
cis-5,11-dihydro-11-[[(2-dimethyl-4-piperidinyl)amino]carbonyl]-6H-pyrido[2,3-b][1,4]benzodiazepin-6-one,
trans-5,11-dihydro-11-[[(1,2-dimethyl-4-piperidinyl)amino]carbonyl]-6H-pyrido[2,3-b][1,4]benzodiazepin-6-one,
cis-5,11-dihydro-11-[[(1,3-dimethyl-4-piperidinyl)amino]carbonyl]-6H-pyrido[2,3-b][1,4]benzodiazepin-6-one,
trans-5,11-dihydro-11-[[(1,3-dimethyl-4-piperidinyl)amino]carbonyl]-6H-pyrido[2,3-b][1,4]benzodiazepin-6-one,
endo-5,11-dihydro-11-[[(8-methyl-8-azabicyclo[3,2,1]oct-3-yl)-amino]-carbonyl]-6H-pyrido[2,3-b][1,4]benzodiazepin-6-one,
exo-5,11-dihydro-11-[[(8-methyl-8-azabicyclo[3,2,1]oct-3-yl)-amino]-carbonyl]-6H-pyrido[2,3-b][1,4]benzodiazepin-6-one,
M.p. 237°–239° C. (methanol).

Example 2

5,11-dihydro-11-[[(N-methyl-N-(1-methyl-4-piperidinyl)amino]carbonyl]-6H-pyrido[2,3-b][1,4]benzodiazepin-6-one 4.3 g (0.015 mol) of 4-chlorocarbonyl-5,11-dihydro-6H-pyrido[2,3-b][1,4]benzodiazepin-6-one, 1.6 g (0.015 mol) of sodium carbonate and 2.56 g (0.02 mol) of 1-methyl-4-methylamino-piperidine were refluxed in 150 ml of anhydrous ethanol for 2 and ½ hours, with stirring. The mixture was filtered while hot, the filtrate was concentrated by evaporation in vacuo and the residue was crystallized from ethyl acetate and then from acetonitrile.

Colorless crystals, M.p. 230.5°–232.0° C.
Yield: 54% of theory.

The following were obtained analogously:
cis-5,11-dihydro-11-[[N-methyl-N-(1,2-dimethyl-4-piperidinyl)amino]carbonyl]-6H-pyrido[2,3-b][1,4]-benzodiazepin-6-one,
trans-5,11-dihydro-11-[[N-methyl-N-(1,2-dimethyl-4-piperidinyl)-amino]carbonyl]-6H-pyrido[2,3-b][1,4]-benzodiazepin-6-one,
cis-5,11-dihydro-11-[[(N-methyl-N-(1,3-dimethyl-4-piperidinyl)-amino]carbonyl]-6H-pyrido[2,3-b][1,4]benzodiazepin-6-one,
trans-5,11-dihydro-11-[[N-methyl-N-(1,3-dimethyl-4-piperidinyl)-amino]carbonyl]-6H-pyrido[2,3-b][1,4]benzodiazepin-6-one,
endo-5,11-dihydro-11-[[N-methyl-N-(8-methyl-8-azabicyclo[3,2,1]-oct-3-yl)amino]carbonyl]-6H-pyrido[2,3-b][1,4]benzodiazepin-6-one, m.p. 277°–279° C. (ethanol),
exo-5,11-dihydro-11-[[N-methyl-N-(8-methyl-8-azabicyclo[3,2,1]oct-3-yl)amino]carbonyl]-6H-pyrido[2,3-b][1,4]benzodiazepin-6-one,
5,11-dihydro-11-[[N-methyl-N-(4-methyl-1-piperaziyl)amino]carbonyl]-6H-pyrido[2,3-b][1,4]benzodiazepin-6-one, M.p. 278°–279° C.

Example 3

5,11-dihydro-11-[[(4-methyl-1-piperazinyl)amino]carbonyl]-6H-pyrido[2,3-b][1,4]benzodiazepin-6-one A mixture of 5.5 g (0.0201 mol) of 11-chlorocarbonyl-5,11-dihydro-6H-pyrido[2,3-b][1,4]benzodiazepin-6-one, 6.9 g (0.06 mol) of 1-amino-4-methylpiperazine and 150 ml of anhydrous dioxane was heated for 30 minutes over a steam bath and the cloudy reaction mixture obtained was then mixed while still hot with 2 g of active charcoal, then filtered and the filtrate obtained was concentrated by evaporation in vacuo. The residue was purified by column chromatography on 300 g of silica gel, using a mixture of dichloromethane, methanol and conc. aqueous ammonia (ratio by volume 800:200:5). The residue remaining after the eluates of interest had been evaporated was recrystallized from ethanol. 1.5 g (19% of theory) of colorless crystals of 5,11-dihydro-11-[[(4-methyl-1-piperazinyl)amino]-carbonyl]-6H-pyrido[2,3-b]-[1,4]benzodiazepin-6-one hydrochloride hydrate was obtained, m.p. 219°–221° C. (D). The salt was dissolved in a little water, made alkaline with the calculated quantity of 10% sodium hydroxide soluion and concentrated by evaporation in vacuo at a bath temperature of 40° C. The residue remaining was taken up in dry tetrahydrofuran and filtered and the solvent was again removed from the filtrate in vacuo. After recrystallization from ethyl acetate, the desired watersoluble, colorless base was obtained in the form of colorless crystals, m.p. 213°–215° C. (D). The following were obtained analogously:

5,11-dihydro-11-[[(3,4-dimethyl-1-piperazinly)amino]-carbonyl]-6H-pyrido[2,3-b][1,4]benzodiazepin-6-one,
5,11-dihydro-11-[[(2,4-dimethyl-1-piperazinyl)amino]-carbonyl]-6H-pyrido[2,3-b][1,4]benzodiazepin-6-one,
endo-5,11-dihydro-11-[[(N-methyl-8-azabicyclo[3,2,-1]oct-3-yl)-amino]-carbonyl]-6H-pyrido[2,3-b][1,4]benzodiazepin-6-one,
5,11-dihydro-11-[[(N-methyl-N-(1-methyl-4-piperidinyl)amino]carbonyl)-6H-pyrido[2,3-b][1,4]benzodiazepin-6-one, M.p. 230.5°–232° C. (acetonitrile).
5,11-dihydro-11-[[N-methyl-N-(3,4-dimethyl-1-piperazinyl)amino]-carbonyl]-6H-pyrido[2,3-b][1,4]benzodiazepin-6-one,
5,11-dihydro-11-[[N-methyl-N-(2,4-dimethyl-1-piperazinyl)amino]-carbonyl]-6H-pyrido[2,3-b][1,4]benzodiazepin-6-one,

Example 4

5,11-dihydro-11-[[(1-methyl-4-piperidinyl)oxy]carbonyl]-6H-pyrido[2,3-b][1,4]benzodiazepin-6-one 4.1 g (0.015 mol) of 11-chlorocarbonyl-5,11-dihydro-6H-pyrido-[2,3-b][1,4]benzodiazepin-6-one were refluxed for two hours with 3.45 g (0.03 mol) of 1-methyl-4-piperidinol in 50 ml of chlorobenzene. After cooling, the reaction solution was diluted by the addition of 200 ml of ethyl acetate and then extracted exhaustively with 15% hydrochloric acid. The combined extracts were neutralized with potassium carbonate, then extracted several times with chloroform and the combined chloroform extracts were concentrated to dryness in vacuo. The residue was purified by column chromtography on silica gel using as eluant a mixture of ethyl acetate and methanol (ratio of volumes=1:1). Colorless crystals were obtained, m.p. 247°–248° C., in a yield of 4.0 g (76% of theory).

The following were obtained analogously:
cis-5,11-dihydro-11-[[(1,2-dimethyl-4-piperidinyl)oxy]-carbonyl]-6H-pyrido[2,3-b][1,4]benzodiazepin-6-one,
trans-5,11-dihydro-11-[[(1,2-dimethyl-4-piperidinyl)oxy]carbonyl]-6H-pyrido[2,3-b][1,4]benzodiazepin-6-one,
cis-5,11-dihydro-11-[[(1,3-dimethyl-4-piperidinyl)oxy]-carbonyl]-6H-pyrido[2,3-b][1,4]benzodiazepin-6-one,
trans-5,11-dihydro-11-[[(1,3-dimethyl-4-piperidinyl)oxy]carbonyl]-6H-pyrido[2,3-b][1,4]benzodiazepin-6-one,
5,11-dihydro-11-[[(4-methyl-1-piperazinyl)-oxy]-carbonyl]-6H-pyrido[2,3-b][1,4]benzodiazepin-6-one,
5,11-dihydro-11-[[(3,4-dimethyl-1-piperazinyl)-oxy]carbonyl]-6H-pyrido[2,3-b][1,4]benzodiazepin-6-one,
5,11-dihydro-11-[[(2,4-dimethyl-1-piperazinyl)oxy]carbonyl]-6H-pyrido[2,3-b][1,4]benzodiazepin-6-one,
endo-5,11-dihydro-11-[[(8-methyl-8-azabicyclo[3,2,-1]oct-3-yl)oxy]carbonyl]-6H-pyrido[2,3-b][1,4]benzodiazepin-6-one, m.p. 200° C. (ethyl acetate),
exo-5,11-dihydro-11-[[(8-methyl-8-azabicyclo[3,2,1]oct-3-yl)-oxy]carbonyl]-6H-pyrido[2,3-b][1,4]benzodiazepin-6-one,

Example 5

5,11-dihydro-11-[[(1-methyl-4-piperidinyl)oxy]carbonyl]-6H-pyrido[2,3-b][1,4]benzodiazepin-6-one 4.9 g (0.0425 mol) of 1-methyl-4-piperidinol were added dropwise to a mixture consisting of 22.5 ml of a 20% solution of phosgene in toluene, 100 ml of dioxane and 4.75 g (0.045 mol) of anhydrous sodium carbonate, with external cooling with ice. The mixture was stirred for a further 60 minutes at ambient temperature, then 9.0 g (0.0428 mol) of 5,11-dihydro-6H-pyrido[2,3-b][1,4]benzodiazepin-6-one were added to the reaction mixture and the resulting mixture was refluxed for 4 hours. It was then filtered, the filtrate was concentrated by evaporation in vacuo and the crude product obtained was purified by column chromatography on 500 g of silica gel using a mixture of ethyl acetate and methanol (ratio of volumes 10:2) as the eluant. After recrystallization from ethyl acetate, the colorless crystals melted at 247°–248° C. and were identical, in their mixed melting point, thin layer chromatogram and IR spectrum, to a product prepared according to Example 4.

Yield: 5.8 g (39% of theory).
The following were obtained analogously:
5,11-dihydro-11-[[(4-methyl-1-piperazinyl)oxy]carbonyl]-6H-pyrido[2,3-b][1,4]benzodiazepin-6-one,
endo-5,11-dihydro-11-[[(8-methyl-8-azabicyclo[3,2,-1]oct-3-yl)oxy]carbonyl]-6H-pyrido[2,3-b][1,4]benzodiazepin-6-one, m.p. 200° C. (ethyl acetate).

Example 6

11-Chlorocarbonyl-5,11-dihydro-6H-pyrido[2,3-b][1,4]benzodiazepin-6-one 42 g (0.2 mol) of 5,11-dihydro-6H-pyrido[2,3-b]-[1,4]benzodiazepin-6-one, dissolved in a mixture of 1.5 liters of dry dioxan and 24 ml of anhydrous pyridine, were added dropwise, within 2 hours, to 300 ml (0.6 mol) of a 20% phosgene solution in toluene, at ambient temperature. The mixture was stirred for a further 2 hours at 60° C., then filtered over activated charcoal and the filtrate was stirred into 6 liters of ice cold water. The viscous precipitate obtained was crystallized by the addition of ether, then suction filtered and suspended several times in ethyl acetate. After recrystallization from acetonitrile, the colorless crystals melted at 260°–261° C.

Yield: 33 g (52% of theory).

The following were obtained analogously:

From 5,11-dihydro-6H-pyrido[2,3-b][1,4]benzodiazepin-6-one and methyl chlorocarbonate in a mixture of dioxan and toluene, 5,11-dihydro-11-methoxycarbonyl-6H-pyrido[2,3-b][1,4]benzodiazepin-6-one was obtained, m.p. 266°–267° C. (D) (from 1,2-dichloroethane);

From 5,11-dihydro-6H-pyrido[2,3-b][1,4]benzodiazepin-6-one and benzyl chlorocarbonate in a mixture of dioxan and toluene, 11-benzyloxycarbonyl-6,11-dihydro-6H-pyrido[2,3-b][1,4]benzodiazepin-6-one was obtained;

From 5,11-dihydro-6H-pyrido[2,3-b][1,4]benzodiazepin-6-one and phenyl chlorocarbonate in a mixture of dioxan and toluene, 5,11-dihydro-11-phenyloxycarbonyl-6H-pyrido[2,3-b][1,4]-benzodiazepin-6-one was obtained.

Example 7

5,11-Dihydro-11-[[(4-methyl-1-piperazinyl)amino]carbonyl]-6H-pyrido[2,3-b][1,4]benzodiazepin-6-one hydrochloride hydrate 1 g of 5,11-dihydro-11-[[(4-methyl-1-piperazinyl)amino]carbonyl]-6H-pyrido[2,3-b][1,4]benzodiazepin-6-one was dissolved in a little ethanol and mixed with ethanolic hydrochloric acid. The mixture was concentrated greatly by evaporation and then acetone was added. The precipitate was recrystallized from ethanol. After air-drying 0.8 g of 5,11-dihydro-11-[[(4-methyl-1-piperazinyl)amino]carbonyl]-6H-pyrido[2,3-b][1,4]benzodiazepin-6-one hydrochloride hydrate were obtained; M.p. 219°–221° C. (D).

The following were obtained analogously:

5,11-dihydro-11-[[(4-methyl-1-piperazinyl)amino]carbonyl]-6H-pyrido[2,3-b][1,4]benzodiazepin-6-one hydrobromide hydrate; M.p. 212°–213° C. (D);

5,11-dihydro-11-[[(4-methyl-1-piperazinyl)amino]carbonyl]-6H-pyrido[2,3-b][1,4]benzodiazepin-6-one maleate hydrate; M.p. 152°–153° C. (D);

5,11-dihydro-11-[[(4-methyl-1-piperazinyl)amino]carbonyl]-6H-pyrido[2,3-b][1,4]benzodiazepin-6-one hemifumarate hydrate; M.p. 159°–160° C. (D);

5,11-dihydro-11-[[(4-methyl-1-piperazinyl)amino]carbonyl]-6H-pyrido[2,3-b][1,4]benzodiazepin-6-one citrate; M.p. 131°–133° C. (D);

5,11-dihydro-11-[[(4-methyl-1-piperazinyl)amino]carbonyl]-6H-pyrido[2,3-b][1,4]benzodiazepin-6-one methanesulfonate; M.p. 239°–240° C. (D);

5,11-dihydro-11-[[(4-methyl-1-piperazinyl)amino]carbonyl]-6H-pyrido[2,3-b][1,4]benzodiazepin-6-one sulfate hydrate; M.p. 192°–193° C. (D);

5,11-dihydro-11-[[(4-methyl-1-piperazinyl)amino]carbonyl]-6H-pyrido[2,3-b][1,4]benzodiazepin-6-one hemitartrate dihydrate; m.p. 165°–166° C. (D);

5,11-dihydro-11-[[(4-methyl-1-piperazinyl)amino]carbonyl]-6H-pyrido[2,3-b][1,4]benzodiazepin-6-one phosphate dihydrate m.p. 280°–281° C. (D).

The preparation of some pharmaceutical forms will now be described with reference to some Examples:

Example I

Tablets containing 5 mg of 5,11-dihydro-11-[[(4-methyl-1-piperazinyl)amino]carbonyl]-6H-pyrido[2,3-b][1,4]benzodiazepin-6-one hydrochloride hydrate Composition:

| Tablet contains: | |
| --- | --- |
| Active substance | 5.0 mg |
| Lactose | 148.0 mg |
| Potato starch | 65.0 mg |
| Magnesium stearate | 2.0 mg |
| | 220.0 mg |

Method of preparation:

A 10% mucilage is prepared from potato starch by heating. The active substance, lactose and remaining potato starch are mixed together and granulated with the mucilage through a screen with a mesh size of 1.5 mm. The granulate is dried at 45° C., passed through the screen again, mixed with magnesium stearate and compressed to form tablets.

Weight of tablet: 220 mg
Die diameter: 9 mm

Example II

Coated tablets containing 5 mg of 5,11-dihydro-11-[[(4-methyl-1-piperazinyl)amino]carbonyl]-6H-pyrido[2,3-b][1,4]benzodiazepin-6-one hydrochloride hydrate The tablets prepared according to Example I are coated by a known method with a shell consisting essentially of sugar and talc. The finished coated tablets are polished with beeswax.

Weight of coated tablet: 300 mg

Example III

Ampoules containing 1 mg of 5,11-dihydro-11-[[(4-methyl-1-piperazinyl)-amino]carbonyl]-6H-pyrido[2,3-b][1,4]benzodiazepin-6-one hydrochloride hydrate Composition:

| 1 ampoule contains: | |
| --- | --- |
| Active substance | 1.0 mg |
| Sodium chloride | 8.0 mg |
| Distilled water qs | 1 ml |

Method of preparation:

The active substance and sodium chloride are dissolved in distilled water and then topped up to the volume given. The solution is sterilely filtered and transferred into 1 ml ampoules.

Sterilisation: 20 minutes at 120° C.

Example IV

Suppositories containing 5 mg of 5,11-dihydro-11-[[(4-methyl-1-piperazinyl)amino]carbonyl]-6H-pyrido[2,3-b][1,4]benzodiazepin-6-one hydrochloride hydrate Composition:

| 1 suppository contains: | |
| --- | --- |
| Active substance | 5.0 mg |

-continued

| | |
|---|---|
| Suppository mass (e.g. Witepsol W 45 ®) | 1695.0 mg |
| | 1700.0 mg |

Method of preparation:

The finely powdered active substance is dispersed in the molten suppository mass which has been cooled to 40° C. At 37° C. the mass is poured into slightly chilled suppository moulds.

Weight of suppository: 1.7 g

Example V

Drops containing 5,11-dihydro-11-[[(4-methyl-1-piperazinyl)amino]-carbonyl]-6H-pyrido[2,3-b][1,4]benzodiazepin-6-one hydrochloride hydrate in a quantity of 0.5 g of active substance per 100 ml of solution Composition:

| 100 ml of drops solution contain: | | |
|---|---|---|
| Methyl p-hydroxybenzoate | 0.035 | g |
| Propyl p-hydroxybenzoate | 0.015 | g |
| Anise oil | 0.05 | g |
| Menthol | 0.06 | g |
| Pure ethanol | 10.0 | g |
| Active substance | 0.5 | g |
| Sodium cyclamate | 1.0 | g |
| Glycerol | 15.0 | g |
| Distilled water qs | 100.0 | ml |

Method of preparation:

The active substance and sodium cyclamate are dissolved in about 70 ml of water and glycerol is added thereto. The p-hydroxybenzoates, anise oil and menthol are dissolved in the ethanol and this solution is added to the aqueous solution with stirring. Finally, the mixture is made up to 100 ml with water and filtered to remove any suspended particles.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A compound of the formula

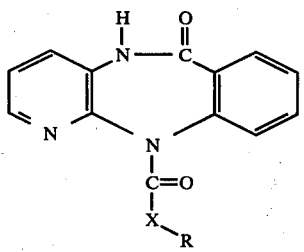

(I)

wherein X is oxygen, —NH—, or —NCH₃— and R is 1-methyl-4-piperidinyl, 4-methyl-1-piperazinyl, or a 3α- or 3β-tropanyl group, each of the groups being optionally substituted by a further methyl group, a diastereomer or enantiomer thereof, or a non-toxic, pharmaceutically acceptable acid addition salt thereof.

2. A compound of claim 1, wherein X is oxygen or —NH— and R is 1-methyl-4-piperidinyl or 4-methyl-1-piperazinyl, or a non-toxic, pharmaceutically acceptable acid addition salt thereof.

3. The compound of claim 1 which is selected from the group consisting of 5,11-dihydro-11-[[(4-methyl-1-piperazinyl)amino]-carbonyl]-6H-pyrido[2,3-b][1,4]benzodiazepin-6-one and the non-toxic, pharmaceutically acceptable acid addition salt thereof.

4. A compound of claim 1 which is selected from the group consisting of 5,11-dihydro-11-[[(1-methyl-4-piperidinyl)oxy]-carbonyl]-6H-pyrido[2,3-b][1,4]-benzodiazepin-6-one and its non-toxic, pharmaceutically acceptable acid addition salts.

5. A compound of claim 1 which is selected from the group consisting of 5,11-dihydro-11-[[(1-methyl-4-piperidinyl)amino]-carbonyl]-6H-pyrido[2,3-b][1,4]-benzodiazepin-6-one and its non-toxic, pharmaceutically acceptable acid addition salts.

6. A compound of the formula

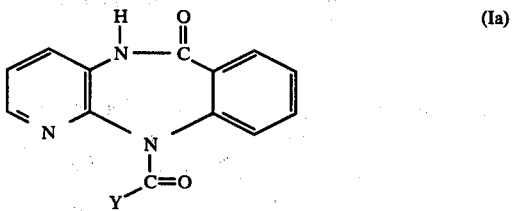

(Ia)

wherein Y is halogen or OR₁, wherein R₁ represents an optionally halogen substituted alkyl group with 1 to 5 carbon atoms, a phenyl group optionally substituted by halogen or nitro, or a benzyl group.

7. The compound of claim 6, wherein Y is chlorine or bromine.

8. A pharmaceutical composition for preventing or treating ulcers in the stomach or intestines of warm-blooded animals which comprises an effective amount of at least one compound of claim 1 together with one or more inert carriers and/or diluents.

9. A method of preventing or treating ulcers in the stomach and intestines of warm-blooded animals comprising administering to warm-blooded animals an amount of at least one compound of claim 1 sufficient to prevent or treat ulcers.

10. A method of claim 9 wherein X is —O— or —NH— and R is 1-methyl-4-piperidinyl or 4-methyl-1-piperazinyl.

11. The method of claim 9 wherein the compound is selected from the group consisting of 5,11-dihydro-11-[[(4-methyl-1-piperazinyl)-amino]-carbonyl]-6H-pyrido-[2,3-b][1,4]benzodiazepin-6-one and its non-toxic, pharmaceutically acceptable acid addition salts.

12. The method of claim 9 which is selected from the group consisting of 5,11-dihydro-11-[[(1-methyl-4-piperidinyl)-oxy]-carbonyl]-6H-pyrido-[2,3-b][1,4]-benzodiazepin-6-one and its non-toxic, pharmaceutically acceptable acid addition salts.

13. The method of claim 9 which is selected from the group consisting of 5,11-dihydro-11-[[(1-methyl-4-piperidinyl)amino]-carbonyl]-6H-pyrido-[2,3-b][1,4]-benzodiazepin-6-one and its non-toxic, pharmaceutically acceptable acid addition salts.

* * * * *

UNITED STATES PATENT AND TRADEMARK OFFICE
CERTIFICATE OF CORRECTION

PATENT NO. : 4,424,222
DATED : January 3, 1984
INVENTOR(S) : WOLFHARD ENGEL et al.

It is certified that error appears in the above-identified patent and that said Letters Patent are hereby corrected as shown below:

Title page [73], the Assignee's name should read
-- Dr. Karl Thomae GmbH --

Column 16, last line of Claim 3: "salt" should read -- salts --.

Column 16, first line of each of Claims 12 and 13: "which" should be deleted, and -- wherein the compound -- should be inserted instead.

Signed and Sealed this

Twelfth Day of February 1985

[SEAL]

*Attest:*

DONALD J. QUIGG

*Attesting Officer*   *Acting Commissioner of Patents and Trademarks*